United States Patent
Gueneron (10) Patent No.: US 9,341,293 B2
(45) Date of Patent: May 17, 2016

(54) CONNECTION HAVING COMMUNICATION BETWEEN BIOPHARMACEUTICAL CONTAINERS AND/OR CONDUITS

(75) Inventor: Mareva Gueneron, Auriol (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 727 days.

(21) Appl. No.: 13/700,213

(22) PCT Filed: Apr. 20, 2011

(86) PCT No.: PCT/FR2011/050916
§ 371 (c)(1),
(2), (4) Date: Nov. 27, 2012

(87) PCT Pub. No.: WO2011/148070
PCT Pub. Date: Dec. 1, 2011

(65) Prior Publication Data
US 2013/0068316 A1   Mar. 21, 2013

(30) Foreign Application Priority Data

May 28, 2010   (FR) ...................................... 10 54172

(51) Int. Cl.
*F16L 27/107*   (2006.01)
*F16L 33/30*   (2006.01)
(Continued)

(52) U.S. Cl.
CPC .............. *F16L 27/107* (2013.01); *A61M 39/10* (2013.01); *F16L 19/00* (2013.01); *F16L 33/30* (2013.01);
(Continued)

(58) Field of Classification Search
CPC ......... F16L 27/107; F16L 19/00; F16L 33/30; F16L 37/04; A61M 39/10; A61M 2039/1088; A61M 2039/1077; A61M 2039/1027; A61M 2039/1083; Y10T 137/0402; Y10T 137/598; F16K 7/06; F16K 7/061; F16K 7/063; F16K 7/065

USPC .................. 285/235, 223; 251/7–10; 403/223
See application file for complete search history.

(56) References Cited

U.S. PATENT DOCUMENTS 1,922,431 A * 8/1933 Geyer ............................ 464/175
3,317,087 A * 5/1967 Landis .......................... 222/143
(Continued)

FOREIGN PATENT DOCUMENTS

DE   20 2008 006416   9/2009
EP   0450700 A1   9/1991
(Continued)

OTHER PUBLICATIONS

International Search Report dated Aug. 4, 2011, corresponding to PCT/FR2011/050916.

*Primary Examiner* — John K Fristoe, Jr.
*Assistant Examiner* — Andrew J Rost
(74) *Attorney, Agent, or Firm* — Young & Thompson (57) ABSTRACT

A connection part providing communication between biopharmaceutical containers and/or conduits, includes a connection sheath (32) and two connection skirts (38a, 38b). The connection sheath (32) and both connection skirts (38a, 38b) have resiliency such that the connection part (30), from a disassembled state, is transversely stretchable, at the site of both connection skirts (38a, 38b) thereof, until transversely widened without loss of integrity so as to be made threadable through both collars (14, 24). Then, due to the resiliency thereof, the connection part contacts, with resilient clamping for support and with sealability, the coupled portion of the outer surface of both collars (14, 24). Moreover, from the assembled state, the connection part is transversely stretchable, at the site of both connection skirts (38a, 38b) thereof, until transversely widened so as to be capable of being unthreaded from both collars (14, 24) and thus be converted to the disassembled state.

17 Claims, 4 Drawing Sheets

(51) Int. Cl.
  *F16L 37/04* (2006.01)
  *F16L 19/00* (2006.01)
  *A61M 39/10* (2006.01)

(52) U.S. Cl.
  CPC ........ *F16L 37/04* (2013.01); *A61M 2039/1027* (2013.01); *A61M 2039/1077* (2013.01); *A61M 2039/1083* (2013.01); *A61M 2039/1088* (2013.01); *Y10T 137/0402* (2015.04); *Y10T 137/598* (2015.04)

(56) References Cited

U.S. PATENT DOCUMENTS

| | | | | |
|---|---|---|---|---|
| 4,524,802 | A * | 6/1985 | Lawrence et al. | 137/595 |
| 4,953,897 | A * | 9/1990 | Klober | 285/226 |
| 5,006,376 | A * | 4/1991 | Arima et al. | 277/636 |
| 5,766,744 | A * | 6/1998 | Fanselow et al. | 428/213 |
| 5,791,696 | A * | 8/1998 | Miyajima et al. | 285/226 |
| 6,653,377 | B1 | 11/2003 | Lloyd et al. | |
| 6,708,377 | B2 | 3/2004 | Maunder | |
| 6,932,346 | B1 | 8/2005 | Hayward | |
| 7,137,611 | B2 * | 11/2006 | Aulicino | 251/9 |
| 7,384,078 | B2 | 6/2008 | Cobb et al. | |
| 2003/0080140 | A1 | 5/2003 | Neas et al. | |
| 2007/0182562 | A1 | 8/2007 | Abbott et al. | |
| 2008/0088326 | A1 * | 4/2008 | Volkerink et al. | 324/754 |
| 2009/0131180 | A1 | 5/2009 | Satoh et al. | |

FOREIGN PATENT DOCUMENTS

| | | |
|---|---|---|
| EP | 0 997 155 | 5/2000 |
| EP | 1 352 851 | 10/2003 |
| EP | 1 230 505 | 7/2008 |
| EP | 1 950 481 | 7/2008 |
| FR | 2 414 144 | 8/1979 |
| WO | 0074735 A1 | 12/2000 |
| WO | 2009/053572 | 4/2009 |
| WO | 2009/118494 | 10/2009 |
| WO | 2010/007273 | 1/2010 |

* cited by examiner

CONNECTION HAVING COMMUNICATION BETWEEN BIOPHARMACEUTICAL CONTAINERS AND/OR CONDUITS

BACKGROUND OF THE INVENTION

1. Field of the Invention

The invention relates to connections (i.e., a physical bond) with communication between biopharmaceutical containers and/or conduits.

2. Description of the Related Art

First of all, the invention more particularly has as its object a connecting part with communication for biopharmacy designed to connect two containers and/or conduits and to bring their inner spaces into communication. Secondly, a unit comprising such a connecting part with communication and at least one blocking clamp, and/or at least one functional means placed at least partially in the inner space of such a part. Thirdly, an assembly that consists of such a connecting part with communication, a first container or conduit, and a second container or conduit. Fourthly, a functional device for implementing a biopharmaceutical process that comprises at least a first container or conduit and a second container or conduit participating in such an assembly. And, fifthly, a process for connecting two containers and/or conduits with communication in biopharmacy.

Here, biopharmacy or biopharmaceutical is defined as that which relates to biotechnology, to pharmacy, and more generally to the medical field. In particular, biopharmaceutical product is defined as a product that is obtained from biotechnology—culture media, cellular cultures, buffer solutions, liquids of artificial nutrition, or a pharmaceutical product or more generally a product that is designed to be used in the medical field, at least in part in solid form that is more or less finely divided, in liquid form, or in paste form.

In biopharmacy, the need exists to be able to connect with communication, in a stationary, removable and sealed manner, parts such as—or parts of—containers and/or conduits, which, if necessary, can be integrated in more or less complex units that can comprise several containers and/or conduits that are combined with one another, and, if necessary, one or more access means in the inner space of such containers and/or conduits and/or one or more functional means. Such functional means are, for example, capable of and designed for treatment of a biopharmaceutical product, for example a means for mixing, aeration, measuring (collecting) data, or pumping, or capable of and designed for support of the containers and/or conduits. Such functional means are, as appropriate, capable of and designed to be placed completely inside or outside or partly inside and partly outside such containers and/or conduits.

Here, "containers" conventionally refers to that which in biopharmacy is capable of and designed in its inner space to contain, encase or enclose certain biopharmaceutical contents or, if necessary, several biopharmaceutical contents, in a more or less long-lasting or permanent static manner. Such biopharmaceutical contents are typically a biopharmaceutical product but can also be a functional means, as defined above. Such containers are, for example, pouches, sheaths, containers, receptacles, bioreactors, or else funnels for biopharmaceutical use, where this list is not limiting.

Such containers, considered collectively, are either rigid or flexible (for example, to be able to be folded flat before use) or partially rigid and partially flexible. As appropriate, they are made of stainless steel or plastic, with these embodiments not being limiting, and their capacity can range from less than one liter to more than 3,000 liters, with these values not being limiting.

Depending on the applications, such containers have a function of storage, shipping, handling, transfer or else bioreaction, where this list is not limiting.

As appropriate, such containers are for multiple use or single use.

SUMMARY OF THE INVENTION

The object of the invention is the case of such containers of the type comprising, in particular toward at least one end, at least one resistant annular collar. Such a collar extends axially toward the outside of the container. Such a collar comprises a terminal radial bulge that extends laterally toward the outside. Such a collar limits toward the inside an opening that allows access to the inner space of the container for the purpose in particular of introducing into, or extracting from, the container, respectively, the or some of the biopharmaceutical contents.

Examples of such containers are described in particular in the documents WO 2009/053572 and WO 2010/007273 and WO 2009/118494.

Here, "conduit" conventionally refers to that which in biopharmacy is capable of and designed for channeling or guiding one or more biopharmaceutical contents and more specially biopharmaceutical products, in its elongated inner space, in such a way as to allow its movement from upstream to downstream. Such conduits are, for example, tubes, ports, drains, pipes, sheaths, or else funnels for biopharmaceutical use, where this list is not limiting.

Such conduits, considered collectively, are either rigid or flexible or partially rigid and partially flexible. As appropriate, they are made of stainless steel or plastic, with these embodiments not being limiting. As appropriate, their length and their diameter, respectively, are more or less large.

Depending on the applications, such conduits have a transfer function, but they can also have a preservation function, for example for sampling, where this list is not limiting.

As appropriate, such pipes are for multiple use or for single use.

The object of the invention is the case of such conduits of the type comprising a rigid annular collar at least one end. Such a collar extends axially toward the outside of the conduit. Such a collar comprises a terminal radial bulge that extends laterally toward the outside. Such a collar limits the opening of the conduit toward the inside.

It is understood that the distinction made above between container and conduit essentially aims to illustrate each of them, not to contrast them, a funnel, for example, able to be seen, according to the time under consideration and the function met, as a container (ensuring a holding function in a location corresponding to the inner space of the funnel) or as a conduit (ensuring a channeling function in the inner space of the funnel). However, in all of the cases, the container or the conduit comprises at least one resistant annular collar that extends toward the outside, comprising a terminal radial bulge that extends laterally toward the outside and that limits an opening of the container or the conduit toward the inside.

Traditionally and as disclosed in the ISO 2852: 1993 standard, it is provided to assemble and to connect two such collars in a stationary, removable and sealed way, by means of a clamp that acts as a flange, comprising two jaws connected between them, for example articulated, and tightening and locking means. Such clamps, also known under the name of "tri-clamp," are the object of numerous variant embodiments, such as those described in particular in the documents EP-A-1230505, U.S. Pat. No. 6,708,377, and U.S. Pat. No. 7,384,078, where this list is not limiting. Such a tri-clamp conventionally comprises a tightening cuff that at each of its two ends has a corresponding bulge, with a tightening element cooperating structurally and functionally with the lateral radial bulges opposite to the first biopharmaceutical container or conduit and the second biopharmaceutical container or conduit. More specifically, the clamp, flange or tri-clamp is capable of and designed to come to be tightened on the first and the second lateral terminal radial bulges by keeping them firmly against one another by their transverse end faces, to prevent their inadvertent disassembly and to ensure sealing. The object of the documents EP-A-0997155 and EP-A-1352851 is the implementation of such clamps or tri-clamps.

These embodiments have a certain number of limits and drawbacks. These tri-clamps, which are conventionally for multiple use, are expensive. They are ill-suited to the increasingly common and desired case of single use (per se or for a process overall). Most often, their inside diameter does not exceed about ten centimeters, whereas more and more frequently, the use of biopharmaceutical devices that are larger in size, in particular involving openings of containers, is considered. Their installation often proves difficult, long and hazardous, to the extent that the operator has to hold the tri-clamp and maneuver it (to close it) and simultaneously hold at least either the first container or conduit and the second container or conduit, and even both, while keeping them perfectly positioned relative to one another. These drawbacks are unacceptable when, as is more and more often desired, the two parts have to be able to be assembled quickly and more easily.

In addition, these embodiments only allow the assembly of a first biopharmaceutical container or conduit and a second biopharmaceutical container or conduit whose respective openings have identical diameters.

The document US-A-2003/0080140 describes a pouch, here of small capacity, having an exit port on which is mounted a connector on which in its turn is mounted a tube.

The document DE 20 2008 006416 U1 describes an outlet in the form of a collar with an annular projection on which a tube is mounted.

The document EP-A-1950481 describes a silicone pipe and a reusable connector for connecting one pipe end to such a silicone pipe.

The document U.S. Pat. No. 6,653,377 describes a system for the transfer of particles using a cartridge unit with multiple O-ring seals that can be mounted either on the unloading port or the loading port of a piece of transformation equipment.

The devices that are the object of these last four documents have a general scope but do not pertain to the application that is more especially targeted by the invention.

Consequently, in the biopharmaceutical field, the need exists for being able to connect with communication, in a stationary, removable and sealed manner, a first collar and a second collar as described above, belonging to a first biopharmaceutical container or conduit and to a second biopharmaceutical container or conduit, respectively, in such a way as to ensure communication between the first opening and the second opening, respectively, of the first biopharmaceutical container or conduit and the second biopharmaceutical container or conduit.

More specifically, this need exists with, as requirements, the possibility of a single use (per se or for a process overall), a low cost, a quick and reliable installation (i.e., mounting or assembly) and disassembly, an airtight mounting or assembly, a possibility of application in the case of a first opening and a second opening having different diameters, being able to reach about 50 centimeters.

Also, in biopharmacy, the need exists to use functional devices of the type comprising a first biopharmaceutical container or conduit and a second biopharmaceutical container or conduit connected to one another with communication, in such a way as to meet the above-mentioned requirements, in particular following a "versatile" design as to applications, functions performed, and diameters of openings. Concerning the biopharmaceutical field, it is also important that the materials that are used are such that the components and devices produced from them keep their integrity during sterilization, for example by γ-radiation, and that the devices that are used meet the approval of the health authorities and are compatible with use in a clean room.

The invention has as its object to meet these needs encountered in biopharmacy.

For this purpose, according to a first aspect, the invention has as its object a connecting part with communication for biopharmacy, capable of being either in a disassembled state or in an assembled state where it is connected to and between a first resistant annular collar and a second resistant annular collar limiting a first opening and a second opening of two containers and/or conduits forming a first inner space and a second inner space and capable of, in the assembled state, being located in a communication configuration where it ensures communication between the two inner spaces of two containers and/or conduits, comprising, forming a whole:

A connecting sheath closed laterally on itself, provided at its first free end part and at its second free end part with a first communication opening and a second communication opening, capable of forming and limiting an inner space for connection in communication by the two openings to the first inner space and to the second inner space of the two containers and/or conduits, At the first free end part of the sheath, a first annular and peripheral outer connecting skirt, whose inner lateral face is capable of coming into contact with elastic tightening for holding and sealing on a part mated to the outer face of the first collar, At the second free end part of the sheath, a second annular and peripheral outer connecting skirt, whose inner lateral face is capable of coming into contact with elastic tightening for holding and sealing on a part mated to the outer face of the second collar, The sheath and the two connecting skirts being integral, made of an inherently airtight material for biopharmacy and having an elasticity such that the connecting part with communication is capable of, on the one hand, starting from the disassembled state, being stretched transversely at the site of its two connecting skirts until it is broadened transversely, without loss of integrity, to be made capable of being threaded onto the two collars, and then, by its elasticity, coming into contact with elastic tightening for holding and sealing on the part mated to the outer face of the two collars and thus being brought into the assembled state, without the necessity for an extrinsic attachment part, and, on the other hand, starting from the assembled state, being stretched transversely at the site of its two connecting skirts until being broadened transversely to be able to be unthreaded from the two collars and thus to be brought into the disassembled state, The connecting part with communication being capable of, in the assembled state and in the communication configuration, allowing location and/or channeling in its inner space of at least certain biopharmaceutical contents (10a) originally located in the inner space of a container or conduit.

This part is such that the inner lateral faces of one and the other of the connecting skirts comprise a cylindrical zone of larger inside diameter adjacent to the sheath, a cylindrical zone of smaller inside diameter adjacent to the free end edge of the connecting part with communication and a tapered zone placed between the cylindrical zone of large inside diameter and the cylindrical zone of smaller inside diameter.

According to one embodiment, the first communication opening and the second communication opening have different diameters. In particular, the first communication opening and the second communication opening have different diameters in a ratio that ranges from 1 to 10.

According to one embodiment, the inner face of the connecting part is essentially without rough spots, reliefs or roughness, and more especially is smooth.

According to one embodiment, the connecting part with communication is capable of being located in a flattened configuration for transverse blocking of at least one transverse blocking zone where the zones opposite the inner face of the sheath are applied against one another and prevent communication on both sides of such a transverse blocking zone.

According to one embodiment, the connecting part with communication comprises a single first and/or second free end part and a single first and/or second connecting skirt, the connecting part with communication being designed to be connected with communication to a single first and/or second collar of a single first and/or second container or conduit.

According to one embodiment, the sheath and the two connecting skirts are made of an inherently anti-static material or a material that is made extrinsically anti-static.

According to one embodiment, the sheath and the two connecting skirts are made of silicone or comprise silicone.

According to one embodiment, the connecting part with communication for biopharmacy is disposable.

According to a second aspect, the invention has as its object a unit that comprises a connecting part with communication for biopharmacy as has just been described and at least one blocking clamp that is capable of being located either in an inactive open configuration or in a closed configuration in which it is capable of coming to be placed around the sheath and being applied to the zones opposite its outer face in at least one transverse blocking zone, in such a way that the zones opposite the inner face of the sheath are applied against one another and prevent communication on both sides of such a transverse blocking zone.

According to a second aspect, the invention has as its object a unit that comprises a connecting part with communication for biopharmacy as was just described and at least one functional means placed at least partially in the inner connecting space.

According to a third aspect, the invention has as its object an assembly that consists of a connecting part with communication for biopharmacy as was just described, a first container or conduit, and a second container or conduit, such that:
  The inner lateral face of the first connecting skirt is in contact with elastic tightening for holding and sealing on a part mated to the outer face of the first collar, without the necessity for an extrinsic attachment part,
  And the inner lateral face of the second connecting skirt is in contact with elastic tightening for holding and sealing on a part mated to the outer face of the second collar, without the necessity for an extrinsic attachment part.

According to one embodiment, the assembly comprises a single first and/or second container or conduit and a connecting part with communication for biopharmacy in the corresponding embodiment of this part.

According to one embodiment, the assembly also comprises at least one functional means placed at least partially in the inner connecting space.

According to a fourth aspect, the invention has as its object a functional device for the implementation of a biopharmaceutical process that comprises at least one first container or conduit and a second container or conduit having to be connected with communication, in which the first container or conduit, the second container or conduit, and a connecting part with communication for biopharmacy as was just described form an assembly such as was just described.

According to a fifth aspect, the invention has as its object a process for connecting with communication in biopharmacy: two containers and/or conduits respectively comprising a first resistant annular collar and a second resistant annular collar limiting a first opening and a second opening, characterized by the fact that:
  There are the first container or conduit and the second container or conduit,
  There is a connecting part with communication for biopharmacy as was just described being in the disassembled state,
  The connecting part with communication is stretched transversely at the site of its two connecting skirts until being broadened transversely to be able to be threaded onto the two collars,
  Then, the connecting part with communication is allowed to come, by its elasticity, into contact with elastic tightening for holding and sealing on the part mated to the outer surface of the two collars and thus to be brought into the assembled state, without the necessity for an extrinsic attachment part.

BRIEF DESCRIPTION OF THE DRAWING FIGURES

Other characteristics and advantages will clearly emerge from the description that is given below, by way of indication and in no way limiting, with reference to the accompanying drawings, in which.

DETAILED DESCRIPTION OF THE INVENTION

Figure 1:
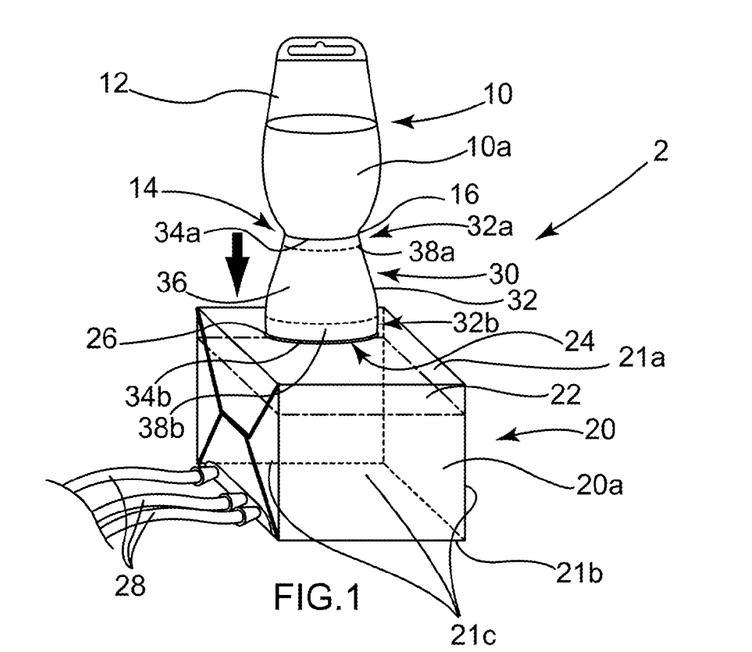
FIG. 1 is a perspective representation of an assembly consisting of a connecting part according to the invention that makes possible communication between a first container and a second container.

FIG. 1 is a perspective view of an assembly 2.

This assembly 2 consists of a first container 10 that forms a transparent and hermetically-sealed flexible pouch that is capable of containing a biopharmaceutical upstream product 10a that is at least partly in more or less finely divided solid form, in liquid form, or in paste form (culture media, cellular cultures, buffer solutions, liquids of artificial nutrition, etc.).

In this case, this first container 10 forms a transparent, flexible pouch. However, this first container 10 could also have a different shape, produced from a solid and non-transparent material.

This first container 10 forms a first inside space 12 and comprises one end on which a first annular collar 14 that limits a first opening 16 is formed.

The assembly 2 of FIG. 1 also comprises a second container 20 that forms a solid and hermetically-sealed 3D pouch inside of which a second inner space 22 is defined that can contain a downstream product 20a such as a liquid, a fluid, or any other type of biopharmaceutical, pharmaceutical or medical product.

This second container 20 comprises an upper surface 21a on which a second annular collar 24 that limits a second opening 26 is formed. The second container 20 has, furthermore, a lower surface 21b opposite to the upper surface 21a as well as four lateral surfaces 21c connecting the upper surface 21a and the lower surface 21b. One of the four lateral surfaces 21c comprises a large number of communication openings that are capable of being connected to the end of transfer pipes 28 so as to transfer in particular downstream product 20a toward secondary containers.

According to a non-limiting embodiment, these transfer pipes 28 can also form a closed circuit that is equipped with a peristaltic pump that makes it possible to circulate and to continually mix the downstream product 20a.

As above, the second container 20 can also have a different shape from the one illustrated in FIG. 1. More particularly, if reference is made to containers 10, 20 with reference to illustrative FIGS. 1 to 7, it should be recalled that the invention is not limited to the connection of such containers but on the contrary extends to the connection of any type of conduits as cited above.

The assembly 2 of FIG. 1 also comprises a connecting part 30 that comprises a connecting sheath 32 that is closed laterally on itself. The connecting sheath 32 is provided at a first free end part 32a with a first communication opening 34a and at a second free end part 32b with a second communication opening 34b. Between its first and second communication openings 34a, 34b, the connecting sheath 32 is capable of forming and limiting an inner connecting space 36.

Advantageously, the connecting sheath 32 has, in the assembled state and in communication configuration, a general cylindrical or tapered shape with a transverse cross-section that is at least approximately circular or pseudo-circular.

It also has an inner face that is essentially without rough spots, reliefs or roughness. This inner face more especially is smooth so as, on the one hand, not to slow down the transfer of the upstream product 10a toward the second container 20, and, on the other hand, not to keep this upstream product 10a inside the connecting part 30.

At the first free end part 32a of the connecting sheath 32, there is formed a first annular and peripheral outer connecting skirt 38a, whose inner lateral face is capable of coming into contact with elastic tightening for holding and sealing on a part that is mated to the outer face of the first collar of the first container 10.

At the second free end part 32b of the connecting sheath 32, there is formed a second annular and peripheral outer connecting skirt 38b, whose inner lateral face is able to come into contact with elastic tightening for holding and sealing on a part that is mated to the outer face of the second collar 24 of the second container 20.

Thus, as FIG. 1 illustrates, the first free end part 32a of the connecting part 32 can be connected to the first annular collar 16 of the first container 10 and the second free end part 32b of the connecting sheath 32 can be connected to the second annular collar 26.

It should be pointed out that the connecting sheath 32 and the first and second connecting skirts 38a, 38b are integral and are formed in an inherently airtight material for biopharmacy. This connecting sheath 32 and these first and second skirts 38a, 38b have an elasticity such that the connecting part 30 is capable of, on the one hand, starting from a disassembled state, being stretched transversely at the site of its two connecting skirts 38a, 38b until being broadened transversely, without loss of integrity, to be made capable of being threaded onto the two annular collars 14, 24 of the first and second containers 10, 20, and then—by its elasticity—coming into contact with elastic tightening for holding and sealing on the part mated to the outer face of the two annular collars 16, 26. Thus, the connecting part 30 can be brought into the assembled state, without the necessity for an extrinsic attachment part. In addition, the connecting sheath 32 and the first and second connecting skirts 38a, 38b have an elasticity such that the connecting part 30 is capable of, on the other hand, starting from the assembled state, being stretched transversely at the site of its two connecting skirts 38a, 38b until being broadened transversely for being able to be unthreaded from the two annular collars 16, 26 and thus being brought into the disassembled state.

So as to connect with communication the first and second containers 10, 20:

- There are the first container 10 and the second container 20,
- There is a connecting part 30 with communication that is in the disassembled state,
- The connecting part 30 with communication is stretched transversely at the site of its two connecting skirts 38a, 38b—successively or simultaneously—until being broadened transversely to be able to be threaded respectively onto the first and second collars 16, 26,
- And then, the connecting part 30 is allowed to come, by its elasticity, into contact with elastic tightening for holding and sealing of the part that is mated to the outer face of the two collars 16, 26 and thus to be brought into the assembled state, without the necessary for an extrinsic attachment part.

In this way, the inner lateral face of the first connecting skirt 38a is in contact with elastic tightening for holding and sealing on a part that is mated to the outer face of the first annular collar 16, without the necessity for an extrinsic attachment part, and the inner lateral face of the second connecting skirt 38b is in contact with elastic tightening for holding and sealing on a part that is mated to the outer face of the second annular collar 26, without the necessity for an extrinsic attachment part.

Furthermore, the connecting part 30 is capable of, in the assembled state and in the communication configuration, allowing location and/or channeling in its inner space of at least one portion of the upstream product 10a that is originally located in the inner space of the first container 10.

It should be emphasized that, according to the embodiment of FIG. 1, the connecting sheath 32 and the first and second connecting skirts 38a, 38b are of a single manufacturing piece. This makes it possible to ensure optimal containment inside the inner connecting space 36, without the risk of leaks linked to the assembly of the connecting sheath 32 with the first and second connecting skirts 38a, 38b.

However, it could also be envisioned that one or the other of the first and second connecting skirts 38a, 38b—and even both—are connected to the connecting sheath 32 by bonding, welding, sewing or any other attachment means making it possible to ensure an adequately hermetically-sealed bond for the communication of biopharmaceutical products.

In contrast, according to an embodiment, the connecting sheath 32 and the first and second connecting skirts 38a, 38b are made of an inherently anti-static material or a material that is made extrinsically anti-static. Thus, the passage of the biopharmaceutical product, in particular when it is powdery inside the inner connecting space 36, is not slowed down because of the inner wall of the connecting sheath 32.

In addition, according to an embodiment, the connecting sheath 32 and the first and second connecting skirts 38a, 38b are made of silicone or partly comprise silicone.

The first container 10, the second container 20, and/or the connecting part 30 can be disposable, which makes it possible to eliminate any cleaning stage after the upstream product 10a has been poured into the second container 20, for example.

Figure 2:
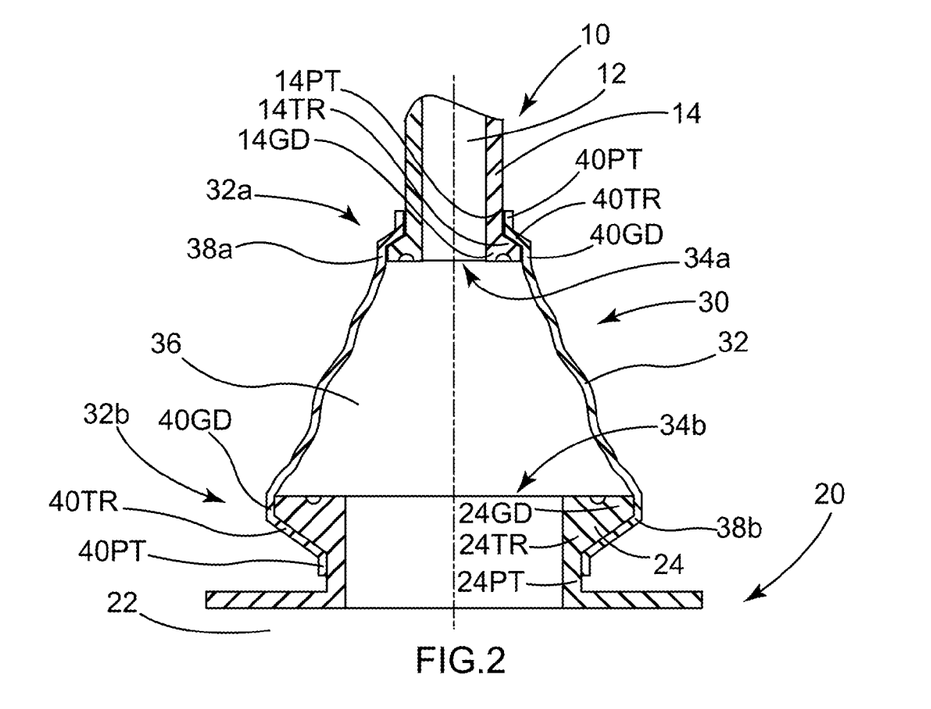
FIG. 2 is a cutaway representation of the assembly of FIG. 1 in which the first collar of the first container is spaced in the vertical direction of the second collar of the second container.

FIG. 2 is now described in detail.

The latter shows, in vertical cutaway, the assembly 2 of FIG. 1 and specifies the structure of the first annular collar 14 and the second annular collar 24.

More particularly, the latter have mechanical characteristics such that it is possible for them to take on the pressures exerted respectively by the first free end part 32a and the second free end part 32b of the connecting sheath 32, without undergoing substantial modification of their geometry. Without this, the hermetic nature of the communication between the first container 10 and the second container 20 could be altered.

According to this embodiment, the inner lateral faces of both of the first and second connecting skirts 38a, 38b comprise a cylindrical zone of larger inside diameter 40GD adjacent to the connecting sheath 32, a cylindrical zone of smaller inside diameter 40PT adjacent to the free end part 32a, 32b of the connecting part 30, and a tapered zone 40TR placed between the cylindrical zone of larger inside diameter 40GR and the cylindrical zone of smaller inside diameter 40PT.

In the same way, the outer surfaces of both the first and second annular collars 14, 24 comprise a cylindrical zone of larger outside diameter 14GR, 24GR, close to their end edge, a cylindrical zone of smaller outside diameter 14PT, 24PT, and a tapered zone 14TR, 24TR placed between the cylindrical zone of larger diameter 14GD, 24GD and the cylindrical zone of smaller outside diameter 14PT, 24PT of the first and second annular collars 14, 24.

Thus, holding the first and second connecting skirts 38a, 38b on the first and second annular collars 14, 24 respectively is ensured not only by the elasticity of the material forming the connecting part 30 but also by the complementary shape of these first and second connecting skirts 38a, 38b with the first and second annular collars 14, 24.

The pressure exerted by the tapered zone 40TR of the first and second connecting skirts 38a, 38b on the tapered zone 14TR, 24TR of the first and second annular collars 14, 24 is thus amplified when the first connecting skirt 38a is removed from the second connecting skirt 38b.

The hermetic nature of the assembly 2 formed in particular by the connecting part 30 is thus supplemented.

According to the embodiment of FIG. 2, the outer lateral faces of both of the connecting skirts 38a, 38b also comprise a cylindrical zone of larger outside diameter 40GR adjacent to the connecting sheath 32, a cylindrical zone of smaller outside diameter 40PT adjacent to the free end edge of the connecting part 30 and a tapered zone 40TR placed between the cylindrical zone of larger outside diameter 40GD and the cylindrical zone of smaller outside diameter 40PT.

In this way, the first connecting skirt 38a and the second connecting skirt 38b comprise an identical or essentially identical radial thickness in the cylindrical zone of larger diameter 40GR, in the cylindrical zone of smaller diameter 40PT, and in the tapered zone 40TR. This makes it possible to simplify the geometry of the connecting part 30 and therefore to facilitate its production.

According to an alternative embodiment, these first and second connecting skirts 38a, 38b could, however, have a larger radial thickness in the cylindrical zone of larger diameter 40GR than in the cylindrical zone of small diameter 40PT and in the tapered zone 40TR. Such an embodiment advantageously makes it possible to reinforce the mechanical properties of the first and second connecting skirts 38a, 38b in this cylindrical zone of larger diameter 40GR so as to make possible its stretching without running the risk of damaging it.

It should also be emphasized that according to the embodiment illustrated by this FIG. 2, both of the connecting skirts 38a, 38b have a tapered zone 40TR. The tapered zone 40TR ensures optimal holding of the connecting skirts 38a, 38b on the first and second annular collars 14, 24.

Furthermore, several different angles could be used.

In contrast, the first communication opening 34a and the second communication opening 34b can have identical or different diameters. For example, the connecting part 30 can act to reduce or expand the diameter for the connection with communication of two containers 10, 20 and/or conduits whose first opening 16 and second opening 26 have different diameters.

According to the embodiment of FIG. 2, the first opening 16 of the first container 10 has a diameter that is smaller than that of the second opening 26 of the second container 20. In the same way, the first communication opening 34a of the first skirt 38a has a diameter that is smaller than that of the second communication opening 34b of the second skirt 38b. Thus, the transfer of the upstream product 10a from the first container 10 and toward the second container 20 does not generate a bottleneck. This difference in diameter is advantageously encompassed in a ratio that ranges from 1 to 10.

In the case where the difference in diameter is adequate, because of the flexibility of the connecting sheath 32, the connecting part 30 is capable of being located when it is not connected to the containers 10, 20:

In a flattened configuration where the zones opposite the inner face of the sheath are applied against one another, and/or In a configuration that is folded like an accordion on itself, with the first free end part 32a and the second free end part 32b of the sheath 32 being brought close together, and even adjacent to one another.

This makes it possible in particular to facilitate the conditioning of these connecting parts 30 by considerably reducing the space necessary for their storage.

It is also possible, however, to produce a first communication opening 34a and a second communication opening 34b having a diameter that is identical or essentially identical for the connection with communication of two containers and/or conduits whose first opening 16 and second opening 26 have a diameter that is identical or essentially identical.

In a general way, furthermore, the first connecting skirt 38a and the second connecting skirt 38b can have, in axial cross-section, an identical or essentially identical shape and an identical or essentially identical axial length, in a ratio that is at least of the same order as the ratio between the diameters of the first communication opening and the second communication opening.

Figure 3:
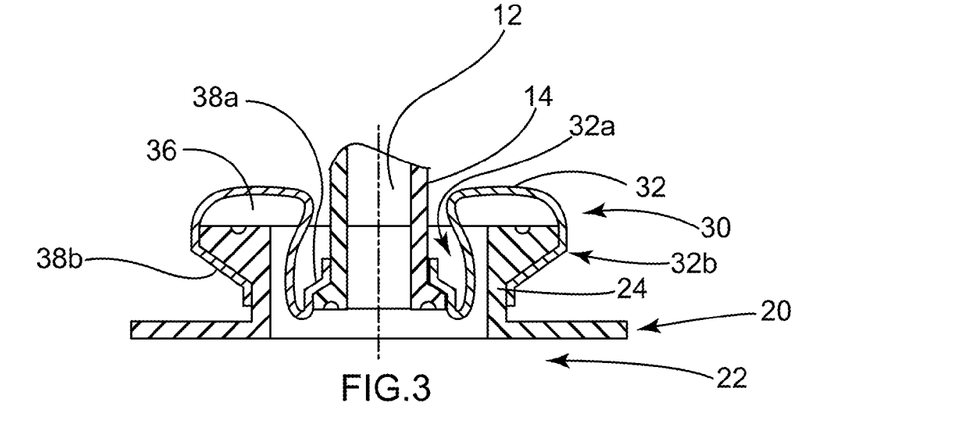
FIG. 3 is a cutaway representation of the assembly of FIG. 1, in which the first collar of the first container is partially introduced into the inner space defined by the second collar of the second container.

The embodiment of FIG. 3 is now described in detail.

The latter is identical to the embodiment of FIG. 1 except for the fact that the first annular collar 14 of the first container 10 is partially introduced into the second inner space 12 defined by the second collar 24 of the second container 20.

According to this embodiment, the connecting sheath 32 has an elasticity such that the first and second skirts 38a, 38b are held in position against the first annular collar 14 and the second annular collar 24 and ensures acceptable sealing in the biopharmaceutical field even when the connecting sheath 32 is not stretched.

According to this embodiment, the connecting sheath 30, because of its flexibility, can then be curved to allow the introduction of the first annular collar 14 of smaller diameter into the second annular collar 24 of larger diameter.

Figure 4:
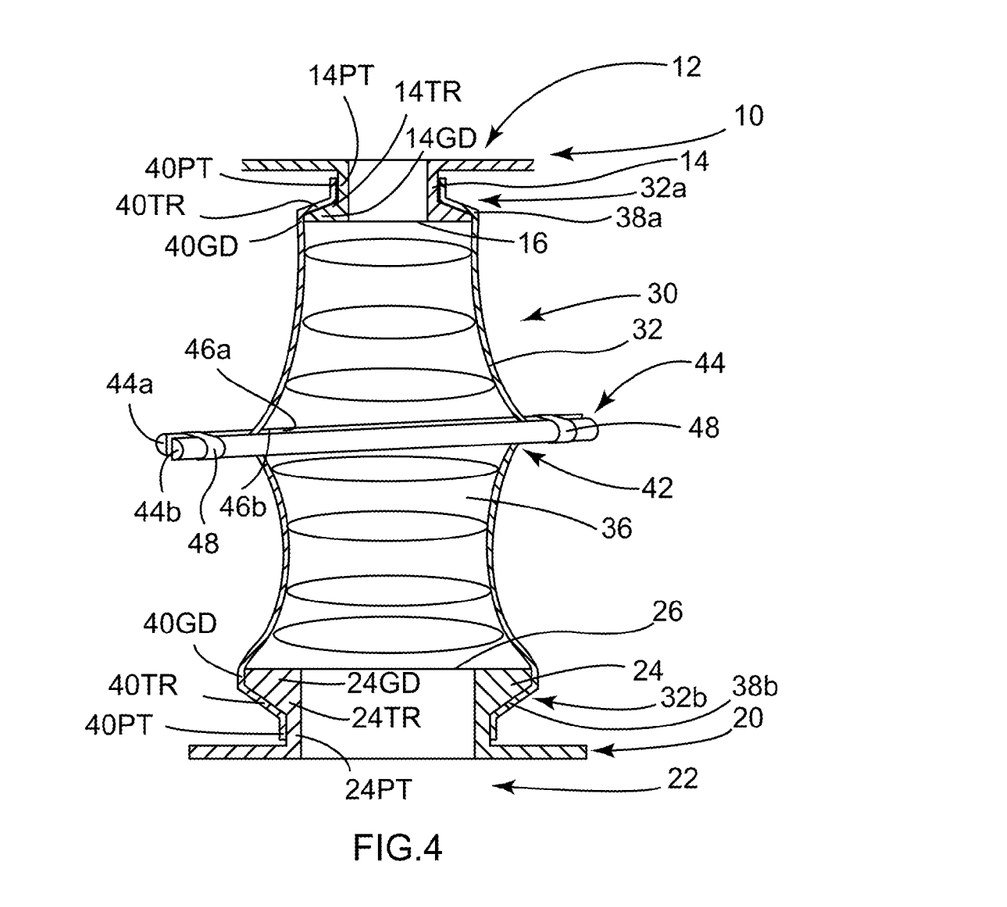
FIG. 4 is a cutaway representation of the assembly of FIG. 1 in which a blocking tool is used to hold the connecting part in a closed configuration in a transverse blocking zone.

The embodiment of FIG. 4 is now described in detail.

This embodiment is also similar to the embodiment of FIG. 1. However, in this case, the connecting part 30 is no longer found in an inactive open position but in a closed blocking configuration in a transverse blocking zone 42. In this closed configuration, the zones opposite the inner face of the connecting sheath 30 are applied against one another and prevent communication on both sides of the transverse blocking zone 42. This embodiment can be used to temporarily prevent the upstream product 10a from flowing through the blocking zone 42 up to the second container 20. It is particularly useful during the preparation of biopharmaceutical products for managing the quantities of upstream products 10a to be used, the filling period of the second container 20, and, for example, stopping the transfer of upstream product 10a toward the second container 20 when the former is filled.

More particularly, in this case depicted, a blocking tool 44 is used that serves to keep adjacent to one another the zones of the inner face of the connecting sheath 30 that are opposite. The blocking tool 44 thus makes it possible, from the outside, to exert stresses on the outer face of the connecting sheath 32 in such a way as to bring close, position facing, and to keep adjacent to one another certain zones opposite the inner face of this connecting sheath 30.

According to this embodiment, this blocking tool 44 comprises two arms 44a, 44b that can move relative to one another, each of them being equipped with a flat association surface 46a, 46b. Thus, the connecting sheath 32 can be obstructed by the blocking tool 44 when it is positioned between these two arms 44a, 44b, and when these two arms 44a, 44b are brought close to one another, and the flat association surfaces 46a, 46b are held against one another.

The blocking tool 44 also comprises holding means 48 that make it possible to hold in a structural and functional way these flat association surfaces 46a, 46b opposite one another in such a way as to prevent communication through the blocking zone 42.

According to the proportions of the connecting part 30, the holding means 48 ensure sealing—acceptable in the biopharmaceutical field—at zones of the inner face of the connecting sheath 32 that are attached.

The blocking tool 44 is not limited to the example that is described and illustrated in FIG. 4 but can, on the contrary, exhibit a different geometry while ensuring sealing of the connecting sheath 32 at the blocking zone 42. In contrast, this blocking zone 42 is not necessarily transverse but can on the contrary extend into an oblique plane relative to the transverse cross-section of the connecting sheath 32.

The blocking tool 44 that can also be a single bar [sic].

Figure 5:
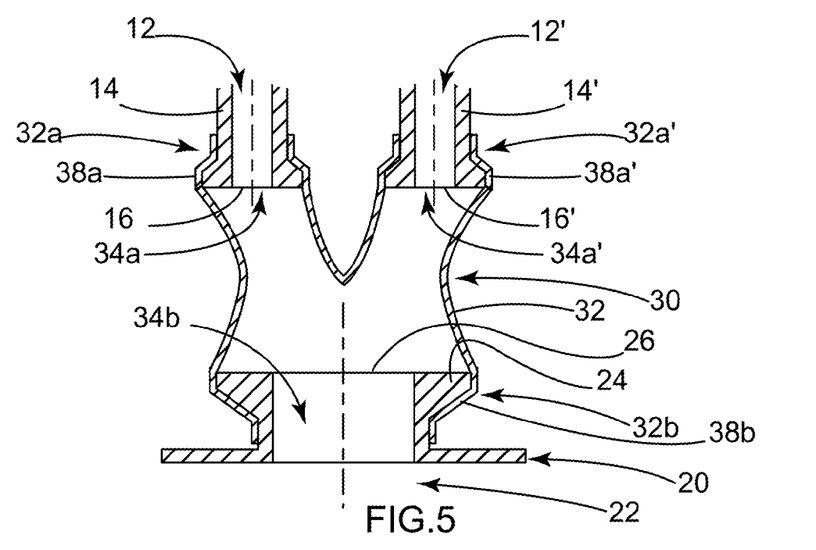
FIG. 5 is a cutaway representation of an assembly that consists of a connecting part according to the invention that makes possible communication between two first containers and a second container.
Figure 6:
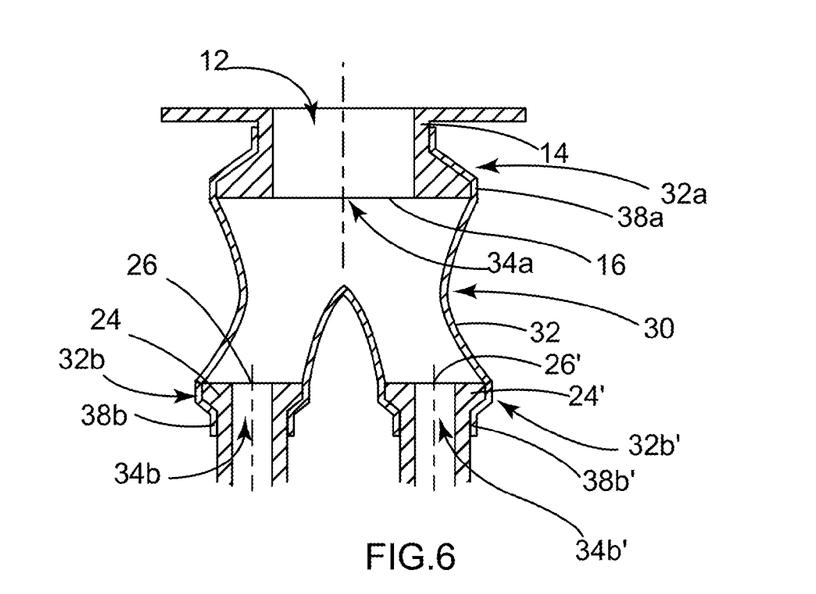
FIG. 6 is a cutaway representation of an assembly that consists of a connecting part according to the invention that makes possible communication between a first container and two second containers.

FIGS. 5 and 6 are now described in a detailed manner.

FIG. 5 illustrates an embodiment that differs from the embodiment of FIG. 1 in that the connecting part 30 does not comprise a first free end part 32a but two first free end parts 32a, 32a'.

As above, each of these two first free end parts 32a, 32a' comprises a first skirt 38a, 38a' and defines a first communication opening 34a, 34a'. This embodiment makes it possible to integrate in the second container 20 upstream products 10a, 10a'—identical or different—that respectively come from two first separate containers 10, 10'.

FIG. 6 illustrates an embodiment that differs from the embodiment of FIG. 1 in that the connecting part 30 comprises not a second free end part 32b but two second free end parts 32b, 32b'.

Just as above, each of these two second free end parts 32b, 32b' comprises a second skirt 38b, 38b' and defines a second communication opening 34b, 34b'. This embodiment makes it possible to integrate—in one stage—an upstream product 10a that originates from the first container 10 into two second containers 20 that are separate from one another.

Of course, according to alternative embodiments, the connecting part 30 may no longer contain two first free end parts 32a, 32a' or two second free end parts 32b, 32b' but x first free end parts 32a, 32a', 32a", etc., or x second free end parts 32b, 32b', 32b" with x greater than two.

This embodiment is particularly advantageous for increasing the rapidity and efficiency of production operation consisting in implementing the transfer of the upstream product(s) 10a that originate from the first container(s) toward the second container(s) 20 for the purpose of forming the downstream product(s) 20a.

The first connecting skirts of the large number of first connecting skirts can be of the same size or essentially the same size or else different sizes relative to one another.

In a similar way, the first sub-sheaths of the large number of first sub-sheaths are:
  Either of the same axial diameter and/or length or essentially of the same axial diameter and/or length;
  Or of axial diameter and/or length that are different from one another.

As FIGS. 1 to 6 illustrate, the connecting part 30 according to the invention can be connected to a first container 10 and to a second container 20 for the purpose of forming a structural and functional unit that makes possible the transfer of upstream product 10a through the connecting part 30 and up to the second container 20. The upstream product 10a that is combined with possible other products present in the second container 20 thus forms the downstream product 20a.

However, the connecting part 30 can also contain a functional means such as an element to be placed at least partially in the inner connecting space 36.

This functional means can be formed by any filtration means, buffer storage means, or connection means, which, associated in a structural and functional way with the connecting part 30, makes possible the transfer according to a suitable operating mode of the upstream product 10a toward the second container 20. According to one embodiment, the functional means can, for example, form a funnel in such a way as to transfer with a dropper the upstream product 10*a* through the connecting part 30. In an alternative or simultaneous way, the functional means can also form a filter that makes it possible to allow the transfer of only one portion of the upstream product 10*a*.

The invention is not limited to the embodiments described above but on the contrary extends to any other embodiment that can be used starting from the general knowledge of one skilled in the art.

In particular, the connecting part 30 does not necessarily have two connecting skirts 38*a*, 38*b* as described with reference to FIGS. 1 to 6. On the contrary, the latter can have connecting skirts 38*a*, 38*b* with alternative geometries that also make it possible to combine the connecting part 30 with the opening of the first or second container 10, 20.

Figure 7:
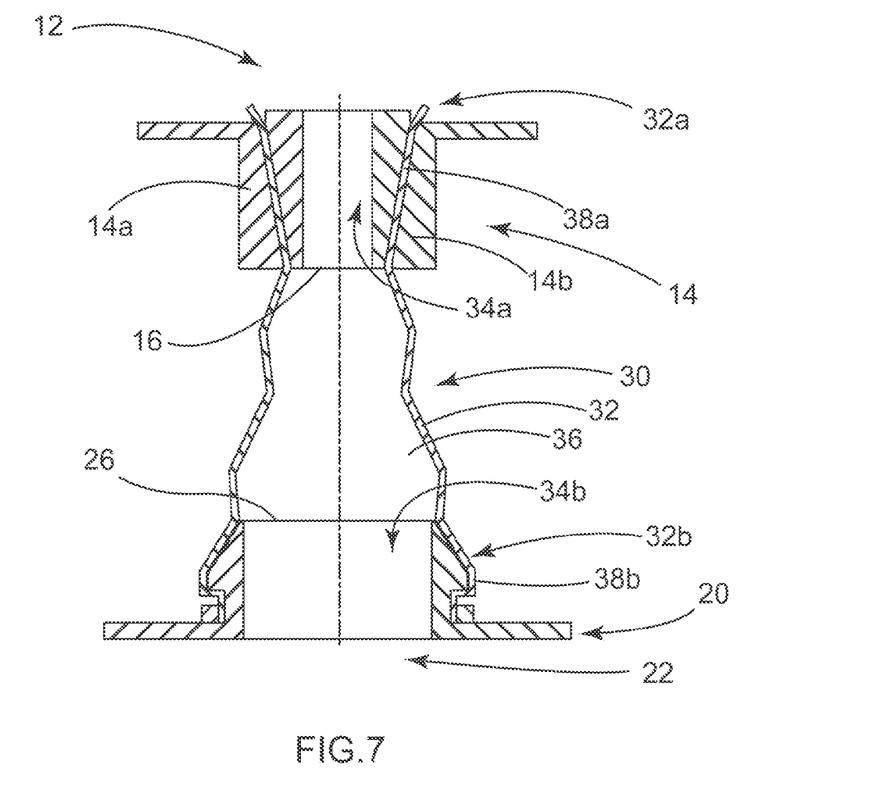
FIG. 7 is a cutaway representation of an assembly that consists of a connecting part according to an alternative embodiment of the invention that makes possible communication between a first container and a second container.

For example, according to an embodiment shown in FIG. 7, the first container 10 can have a first annular collar 14 that is formed by a first annular part 14*a* with a tapered outside diameter and a second annular part 14*b* also with a tapered outside diameter. The first annular part 14*a* has a larger outside diameter on the portion that is oriented toward the first inner space 12 than on the portion oriented toward the outside, while the second annular part 14*b* has a larger outside diameter on the portion that is oriented toward the outside than on the portion oriented toward the first inner space 12.

The first annular part 14*a* also has a mean diameter that is very slightly less than the mean diameter of the second annular part 14*b*. In this way, this first annular part 14*a* can be fitted into the second annular part 14*b* in such a way as to maintain the first connecting skirt 38*a*, previously threaded on the first annular part 14*a* by transverse broadening without loss of integrity relative to the first opening 16 of the first container 10.

This configuration can furthermore be adapted either to the first annular collar 14 of the first container 10 or to the second annular collar 24 of the second container 20, or else to the two annular collars 14, 24.

The invention claimed is:

1. A connecting part for biopharmacy, between a first container or conduit and a second container or conduit for the transfer of a certain biopharmaceutical product from the first container or conduit to the second container or conduit, forming a whole:
    a connecting sheath closed laterally on itself, provided at its first free end part and at its second free end part with a first communication opening and a second communication opening, capable of forming and limiting an inner connecting space,
    at the first free end part, a first annular and peripheral outer connecting skirt, whose inner lateral face is capable of coming into contact with elastic tightening for holding and sealing on a part mated to the outer face of a first collar,
    at the second free end part, a second annular and peripheral outer connecting skirt, whose inner lateral face is capable of coming into contact with elastic tightening for holding and sealing on a part mated to the outer face of a second collar,
    the sheath and the skirts being integral, made of an inherently airtight material for biopharmacy and having an elasticity such that the connecting part is capable of being stretched transversely at the site of the two skirts and, by elasticity, coming into contact with elastic tightening for holding and sealing on the part mated to the outer face of the collars, without the necessity for an extrinsic attachment part,
    the connecting part being capable of, in the assembled state with the first container or conduit and the second container or conduit and in a communication configuration, allowing transfer of the biopharmaceutical product from the first container or conduit to the second container or conduit, wherein
    the inner face of the connecting part is essentially without rough spots, reliefs or roughness so as not to slow down the transfer of biopharmaceutical product and not to keep the product inside the connecting part,
    the connecting sheath has, in the assembled state and in a communication configuration, a general cylindrical or tapered shape,
    the inner lateral faces of one and the other of the skirts comprise a cylindrical zone of larger inside diameter adjacent to the sheath, a cylindrical zone of smaller inside diameter adjacent to the free end edge of the connecting part, and a tapered zone placed between the cylindrical zone of larger inside diameter and the cylindrical zone of smaller inside diameter.

2. The connecting part according to claim 1, wherein the first opening and the second opening have different diameters.

3. The connecting part according to claim 2, wherein the first opening and the second opening have diameters in a ratio that ranges from 1 to 1 (1:1) at one end of the range and 1 to 10 (1:1) at the other end of the range.

4. The connecting part according to claim 1, wherein its inner face is essentially without rough spots, reliefs or roughness, and is smooth.

5. The connecting part according to claim 1, wherein the connecting part is capable of being located in a flattened transverse blocking configuration in at least one transverse blocking zone where the zones opposite the inner face of the sheath are applied against one another and prevent communication on both sides of such a transverse blocking zone.

6. A unit comprising the connecting part according to claim 5, further comprising at least one blocking clamp that can be found either in an inactive open configuration or in a closed configuration in which it is able to come to be placed around the sheath and to be applied to zones opposite an outer face in at least one transverse blocking zone, in such a way that the zones opposite the inner face of the sheath are applied against one another and prevent communication on both sides of such a transverse blocking zone.

7. The connecting part according to claim 1, further comprising a single first and/or second free end part and a single first and/or second skirt, with the connecting part being designed to be connected with communication to a single first and/or second collar of a single first and/or second container or conduit.

8. The connecting part according to claim 1, wherein the sheath and the two skirts are made of an inherently anti-static material or a material that is made extrinsically anti-static.

9. The connecting part according to claim 1, wherein the sheath and the two skirts are made of silicone or comprise silicone.

10. The connecting part according to claim 1, wherein the connecting part is disposable.

11. Unit comprising a connecting part according to claim 1, further comprising at least one functional means that is placed at least partially in the inner connecting space.

12. Assembly that comprises the connecting part according to claim 1, a first container or conduit, and a second container or conduit, such that:
    the inner lateral face of the first connecting skirt is in contact with elastic tightening for holding and sealing on a part mated to the outer face of the first collar, without the necessity for an extrinsic attachment part, and the inner lateral face of the second connecting skirt is in contact with elastic tightening for holding and sealing on a part mated to the outer face of the second collar, without the necessity for an extrinsic attachment part.

13. The assembly according to claim 12, wherein the sheath and the two skirts are made of an inherently anti-static material or a material that is made extrinsically anti-static.

14. The assembly according to claim 13, further comprising at least one functional means placed at least partially in the inner connecting space.

15. The assembly according to claim 12, further comprising at least one functional means placed at least partially in the inner connecting space.

16. A functional device for the implementation of a biopharmaceutical process comprising at least a first container or conduit and a second container or conduit having to be connected with communication, in which the first container or conduit, the second container or conduit, and the connecting part according to claim 1 form an assembly.

17. A process for connecting with communication in biopharmacy two containers and/or conduits comprising, respectively, a first resistant annular collar and second resistant annular collar limiting a first opening and a second opening, wherein:
- there are the first container or conduit and the second container or conduit,
- there is the connecting part according to claim 1 that is in the disassembled state,
- the connecting part is stretched transversely at the site of its two connecting skirts until being broadened transversely to be able to be threaded onto the two collars,
- then, the connecting part is allowed to come, by elasticity, into contact with elastic tightening for holding and sealing on the part mated to the outer face of the two collars and thus to be brought into the assembled state, without the necessity for an extrinsic attachment part.

* * * * *